US012751742B2

(12) United States Patent
Biedermann et al.

(10) Patent No.: US 12,751,742 B2
(45) **Date of Patent: *Oct. 6, 2026**

(54) BONE ANCHORING DEVICE AND TOOL COOPERATING WITH SUCH A BONE ANCHORING DEVICE

(71) Applicant: BIEDERMANN TECHNOLOGIES GMBH & CO. KG, Donaueschingen (DE)

(72) Inventors: Lutz Biedermann, VS-Villingen (DE); Timo Biedermann, Trossingen (DE); Wilfried Matthis, Weisweil (DE); Berthold Dannecker, St. Georgen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/819,339

(22) Filed: Aug. 29, 2024

(65) Prior Publication Data

US 2025/0057568 A1 Feb. 20, 2025

Related U.S. Application Data

(63) Continuation of application No. 17/956,575, filed on Sep. 29, 2022, now Pat. No. 12,096,962, which is a (Continued)

(30) Foreign Application Priority Data

Sep. 30, 2011 (EP) .................................... 11183616

(51) Int. Cl.
*A61B 17/70* (2006.01)

(52) U.S. Cl.
CPC ...... *A61B 17/7035* (2013.01); *A61B 17/7076* (2013.01)

(58) Field of Classification Search
CPC . A61B 17/70; A61B 17/7001; A61B 17/7032; A61B 17/7034; A61B 17/7035;
(Continued)

(56) References Cited

U.S. PATENT DOCUMENTS 5,375,956 A * 12/1994 Pennig ............... A61B 17/8605 411/397
5,549,608 A * 8/1996 Errico ................ A61B 17/7037 606/264

(Continued)

FOREIGN PATENT DOCUMENTS

CN 2803295 Y 8/2006
CN 202637097 U 1/2013

(Continued)

OTHER PUBLICATIONS

European Search Report for European Application No. 11183616.9, European Search Report dated Feb. 8, 2012 and mailed Feb. 17, 2012 (6 pgs.).

*Primary Examiner* — Eric S Gibson
(74) *Attorney, Agent, or Firm* — Womble Bond Dickinson (US) LLP

(57) ABSTRACT

A bone anchoring device includes a receiving part including a rod receiving portion with a first end, a second end, and a U-shaped recess for receiving a rod, the recess defining two free legs, and a head receiving portion at the second end for introducing and clamping the head, and a locking ring configured to be arranged around the head receiving portion, the locking ring including an engagement structure for engagement with a tool, the engagement structure defining a width of the locking ring that is greater than a greatest width of the rod receiving portion, wherein the locking ring
(Continued)

can assume a locking position exerting a greatest compressive force on the head receiving portion of the receiving part to lock an inserted head, and wherein the locking ring is movable out of the locking position towards the first end of the rod receiving portion.

21 Claims, 13 Drawing Sheets

Related U.S. Application Data continuation of application No. 16/937,302, filed on Jul. 23, 2020, now Pat. No. 11,484,347, which is a continuation of application No. 16/173,659, filed on Oct. 29, 2018, now Pat. No. 10,751,092, which is a continuation of application No. 15/597,018, filed on May 16, 2017, now Pat. No. 10,136,922, which is a continuation of application No. 14/845,048, filed on Sep. 3, 2015, now Pat. No. 9,681,895, which is a continuation of application No. 13/631,503, filed on Sep. 28, 2012, now Pat. No. 9,144,441.

(60) Provisional application No. 61/541,511, filed on Sep. 30, 2011.

(58) Field of Classification Search
CPC ............ A61B 17/7043; A61B 17/7074; A61B 17/7076; A61B 17/7082
USPC ........................ 606/86 A, 264–270, 305–308
See application file for complete search history.

(56) References Cited

U.S. PATENT DOCUMENTS 5,575,792 A * 11/1996 Errico ................ A61B 17/7037 606/272
5,586,984 A * 12/1996 Errico ................ A61B 17/7037 606/264
5,672,176 A 9/1997 Biedermann et al.
5,882,350 A 3/1999 Ralph et al.
6,248,105 B1 6/2001 Schläpfer et al.
6,254,602 B1 * 7/2001 Justis ................. A61B 17/7032 606/53
6,273,888 B1 * 8/2001 Justis ...................... F16B 19/00 606/911
6,299,616 B1 * 10/2001 Beger ................ A61B 17/7044 606/86 R
6,582,436 B2 * 6/2003 Schlapfer ........... A61B 17/7037 606/267
6,743,231 B1 * 6/2004 Gray .................. A61B 17/7091 606/279
7,090,674 B2 * 8/2006 Doubler ............. A61B 17/7041 606/277
7,947,065 B2 * 5/2011 Hammill, Sr. ..... A61B 17/7037 606/267
7,955,359 B2 6/2011 Matthis et al.
8,075,603 B2 * 12/2011 Hammill, Sr. ..... A61B 17/7037 606/267
8,192,470 B2 * 6/2012 Biedermann ...... A61B 17/7037 606/267
8,298,275 B2 * 10/2012 Rezach .............. A61B 17/7038 606/267
8,388,659 B1 3/2013 Lab et al.
8,506,609 B2 * 8/2013 Biedermann ...... A61B 17/7037 606/306
8,506,610 B2 * 8/2013 Biedermann ...... A61B 17/7035 606/267
8,556,938 B2 10/2013 Jackson et al.
8,636,781 B2 * 1/2014 Biedermann ...... A61B 17/7035 606/279
8,636,782 B2 * 1/2014 Biedermann ...... A61B 17/7037 606/279
8,888,827 B2 11/2014 Harper et al.
8,926,671 B2 1/2015 Biedermann et al.
8,951,294 B2 2/2015 Gennari et al.
9,144,441 B2 * 9/2015 Biedermann ...... A61B 17/7076
9,155,567 B2 10/2015 Auerbach et al.
9,247,965 B2 2/2016 Biedermann et al.
9,277,938 B2 3/2016 Biedermann et al.
9,603,627 B2 3/2017 Krüger
9,681,895 B2 * 6/2017 Biedermann ...... A61B 17/7035
9,839,446 B2 12/2017 Biedermann et al.
10,136,922 B2 * 11/2018 Biedermann ...... A61B 17/7035
10,258,383 B2 * 4/2019 Biedermann ...... A61B 17/7086
10,271,877 B2 4/2019 Biedermann et al.
10,426,521 B2 10/2019 Mosnier et al.
10,751,092 B2 * 8/2020 Biedermann ...... A61B 17/7076
11,484,347 B2 * 11/2022 Biedermann ...... A61B 17/7076
12,096,962 B2 * 9/2024 Biedermann ...... A61B 17/7035
2004/0097933 A1 5/2004 Lourdel et al.
2004/0254576 A1 * 12/2004 Dunbar, Jr. ........... A61F 2/4611 606/279
2005/0096653 A1 * 5/2005 Doubler ............. A61B 17/7037 606/277
2005/0228385 A1 * 10/2005 Lott .................. A61B 17/7032 606/302
2006/0074445 A1 4/2006 Gerber et al.
2006/0173454 A1 8/2006 Spitler et al.
2006/0247658 A1 * 11/2006 Pond .................. A61B 17/7082 606/104
2007/0049933 A1 3/2007 Ahn et al.
2007/0161987 A1 * 7/2007 Capote ................. A61B 17/704 606/86 A
2007/0167949 A1 7/2007 Altarac et al.
2007/0270842 A1 * 11/2007 Bankoski ............. A61B 17/865 606/86 A
2008/0004625 A1 1/2008 Runco et al.
2008/0015576 A1 1/2008 Whipple
2008/0108992 A1 5/2008 Barry et al.
2008/0161859 A1 * 7/2008 Nilsson ................ A61B 17/704 606/266
2009/0036934 A1 * 2/2009 Biedermann ...... A61B 17/7037 606/301
2009/0062860 A1 * 3/2009 Frasier ................. A61B 17/701 606/264
2009/0105715 A1 * 4/2009 Belliard ............. A61B 17/7053 606/103
2009/0105756 A1 * 4/2009 Richelsoph ........ A61B 17/7035 606/301
2009/0149887 A1 * 6/2009 Schlaepfer ......... A61B 17/7091 606/301
2010/0030135 A1 * 2/2010 Mitchell ............... A61M 31/00 606/305
2010/0114108 A1 5/2010 Strauss
2010/0131017 A1 * 5/2010 Farris ................. A61B 17/7038 606/308
2010/0152787 A1 6/2010 Walsh et al.
2010/0160977 A1 6/2010 Gephart et al.
2010/0168800 A1 * 7/2010 Biedermann ...... A61B 17/7037 606/305
2010/0168801 A1 7/2010 Biedermann et al.
2010/0204735 A1 * 8/2010 Gephart ............. A61B 17/7037 606/279
2010/0234902 A1 9/2010 Biedermann et al.
2011/0060374 A1 3/2011 Sicvol et al.
2011/0125196 A1 * 5/2011 Quevedo .............. A61B 17/701 606/308
2011/0276098 A1 * 11/2011 Biedermann ...... A61B 17/7037 606/1
2012/0046699 A1 * 2/2012 Jones ................. A61B 17/7037 606/305
2012/0046701 A1 2/2012 Gennari et al.
2012/0059426 A1 * 3/2012 Jackson ................. A61B 17/68 606/305
2012/0095516 A1 4/2012 Dikeman
2012/0179209 A1 * 7/2012 Biedermann ...... A61B 17/7037 606/279

(56) References Cited

U.S. PATENT DOCUMENTS

2012/0179211 A1 7/2012 Biedermann et al.
2012/0203288 A1 8/2012 Lange et al.
2012/0209332 A1* 8/2012 Janowski ........... A61B 17/7082 606/278
2012/0283789 A1* 11/2012 Biedermann ...... A61B 17/7034 606/308
2013/0079833 A1 3/2013 Biedermann et al.
2013/0085536 A1* 4/2013 Biedermann ...... A61B 17/7035 606/328
2013/0096622 A1 4/2013 Biedermann et al.
2013/0096623 A1 4/2013 Biedermann et al.
2013/0110179 A1 5/2013 Barrus et al.
2013/0123860 A1* 5/2013 Biedermann ...... A61B 17/8685 606/86 R
2013/0123861 A1* 5/2013 Biedermann ...... A61B 17/8605 606/305
2014/0012337 A1 1/2014 Biedermann et al.
2014/0031880 A1* 1/2014 Biedermann ...... A61B 17/8605 606/305
2014/0188173 A1 7/2014 Mishra et al.
2014/0236239 A1 8/2014 Biedermann et al.
2014/0257411 A1 9/2014 Rezach
2015/0080960 A1 3/2015 Biedermann et al.
2015/0134006 A1 5/2015 Ziolo et al.
2015/0182265 A1 7/2015 Biedermann et al.
2016/0066957 A1* 3/2016 Biedermann ...... A61B 17/7076 606/86 A
2016/0220281 A1 8/2016 Biedermann et al.
2017/0020574 A1* 1/2017 Biedermann ...... A61B 17/7086
2017/0181776 A1 6/2017 Beretta et al.
2017/0319239 A1* 11/2017 Biedermann ...... A61B 17/7035
2018/0132903 A1 5/2018 Biedermann et al.
2019/0125411 A1* 5/2019 Biedermann ...... A61B 17/7076
2021/0000513 A1* 1/2021 Biedermann ...... A61B 17/7076
2023/0093687 A1* 3/2023 Biedermann ...... A61B 17/7035 606/86 A
2025/0057568 A1* 2/2025 Biedermann ...... A61B 17/7076

FOREIGN PATENT DOCUMENTS

CN 103976785 A 8/2014
CN 104434283 A 3/2015
EP 2 851 021 A1 3/2015
FR 2 920 663 A1 3/2009
JP 2007-506525 A 3/2007
WO WO 2005/030070 A1 4/2005
WO WO 2011/043799 A1 4/2011
WO WO 2011/077511 A1 6/2011
WO WO 2015/069873 5/2015

* cited by examiner

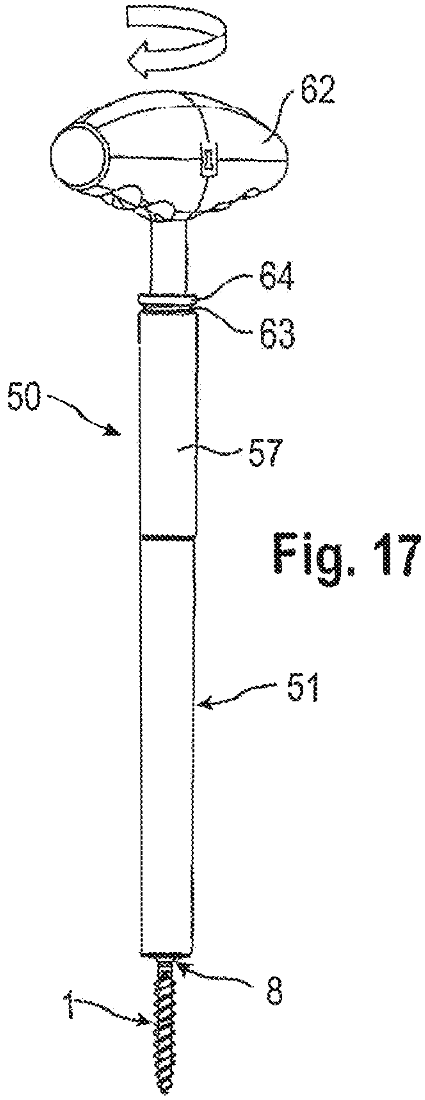
Fig. 17
Fig. 18
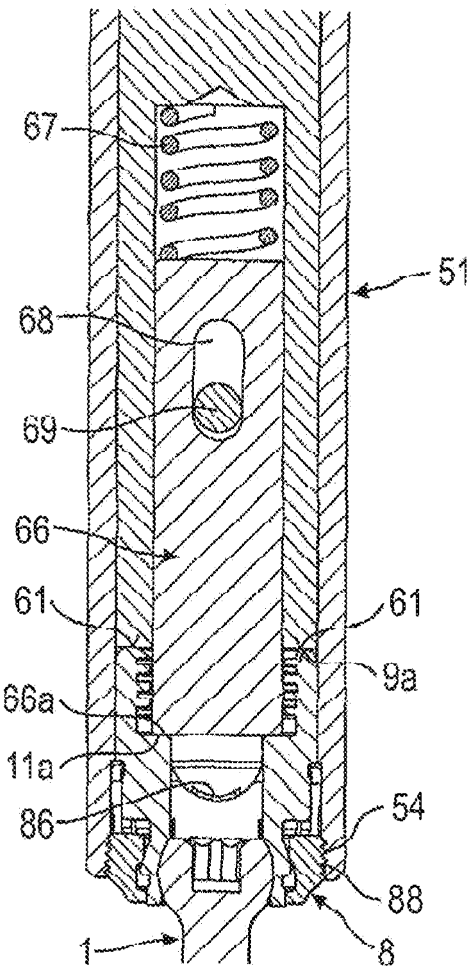
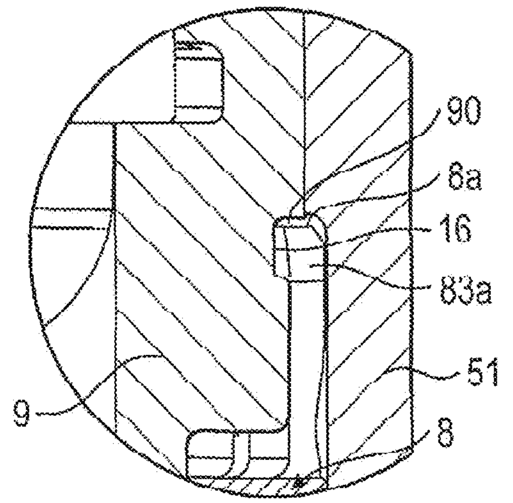
Fig. 19

BONE ANCHORING DEVICE AND TOOL COOPERATING WITH SUCH A BONE ANCHORING DEVICE

CROSS-REFERENCE TO RELATED APPLICATION(S)

This application is a continuation of U.S. patent application Ser. No. 17/956,575, filed Sep. 29, 2022, which is a continuation of U.S. patent application Ser. No. 16/937,302, filed Jul. 23, 2020, now U.S. Pat. No. 11,484,347, which is a continuation of U.S. patent application Ser. No. 16/173,659, filed Oct. 29, 2018, now U.S. Pat. No. 10,751,092, which is a continuation of U.S. patent application Ser. No. 15/597,018, filed May 16, 2017, now U.S. Pat. No. 10,136,922, which is a continuation of U.S. patent application Ser. No. 14/845,048 filed Sep. 3, 2015, now U.S. Pat. No. 9,681,895, which is a continuation of U.S. patent application Ser. No. 13/631,503, filed Sep. 28, 2012, now U.S. Pat. No. 9,144,441, which claims priority to and the benefit of U.S. Provisional Patent Application Ser. No. 61/541,511, filed Sep. 30, 2011, the contents of which are hereby incorporated by reference in their entirety. This application also claims priority to and the benefit of European Patent Application No. EP 11 183 616.9, filed Sep. 30, 2011, the entire content of which is herein incorporated by reference.

BACKGROUND

Field of the Invention

The invention relates to a bone anchoring device including a bone anchoring element and a receiving part for coupling a rod to the bone anchoring element. The receiving part includes a rod receiving portion for receiving the rod and a head receiving portion that is flexible so as to allow introduction and clamping of a head of the bone anchoring element. The bone anchoring device further includes a locking ring arranged around the head receiving portion that can assume a locking position in which an inserted head is locked by compression of the head receiving portion of the receiving part. The locking ring has an outer surface with an engagement portion for engagement with a tool. The tool is configured to cooperate with the receiving part and the locking ring so as to allow releasing of the locking ring from a position in which the locking ring locks the head. The bone anchoring device can be realized, for example, in the form of a polyaxial bone screw.

Description of Related Art

US 2009/0149887 A1 discloses an apparatus for connecting a bone anchor to a support rod, the apparatus including a connector body and a cap. The connector body has a socket for insertion, angulation and removal of a bone anchor. A sleeve is provided, which is configured to fit over the connector body in a temporary position, in which the sleeve permits insertion of the bone anchor, to move to a provisional locking position, in which the sleeve permits angulation but prevents removal of the bone anchor, and to move to a locking position in which the sleeve prevents both angulation and removal of the bone anchor. Tools are provided for installing the connector body, the sleeve, a cap and the support rod.

SUMMARY

It is an object of the invention to provide a bone anchoring device that makes use of an outer locking ring for compressing a head receiving portion to lock a head of a bone anchoring element therein, that is improved with respect to its handling. Further, a tool can be provided that allows or facilitates such improved handling.

The bone anchoring device according to embodiments of the invention provide for safer loosening of a locking mechanism of the device. Also, the bone anchoring device according to embodiments of the invention enables a surgeon or other practitioner to carry out revisions or further positioning or repositioning of the angular positioning of a receiving part with respect to the bone anchoring element. In one embodiment, a releasing of the locking mechanism may be possible with a rod still inserted.

The tool according to embodiments of the invention is configured to engage the receiving part and to be operated along a central axis of the receiving part. Therefore, it will not be necessary to have additional space for laterally applying the tool. Furthermore, the tool will not be jammed by, for example, forces acting only from one side.

Therefore, handling of the bone anchoring device can be simplified, because once a locking of the head is achieved, such locking can be released without applying larger forces that could result in damage to surrounding material, such as tissue, blood vessels, or nerves. Revisions or secondary adjustments of the rod and the receiving part can thus be performed in a more controlled manner.

With the bone anchoring device according to embodiments of the invention, a modular system can be provided that allows for combining of various anchoring elements with any suitable receiving part on demand, depending on the actual clinical requirements. This reduces the overall costs of using polyaxial screws, reduces inventory, and gives the surgeon a wider or more versatile choice of implants.

BRIEF DESCRIPTION OF THE DRAWINGS

Further features and advantages of the invention will become apparent from the description of embodiments by means of the accompanying drawings. In the drawings:

FIG. 17 shows a perspective view of a further step of mounting the tool of FIGS. 11 and 12 to the bone anchoring device of FIGS. 1 and 2;

FIG. 18 shows an enlarged cross-sectional view of a portion of the tool mounted to the bone anchoring device as shown in FIG. 17;

FIG. 19 shows a further enlarged portion of FIG. 18;

DETAILED DESCRIPTION

Figure 1:
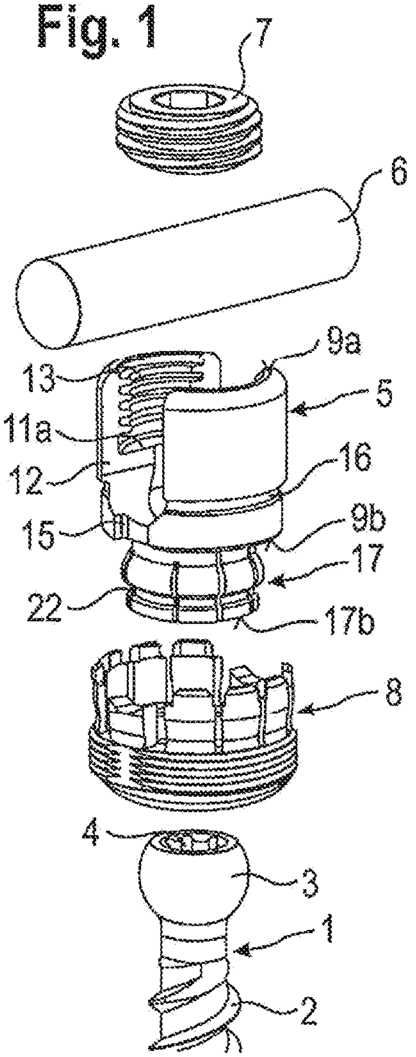
FIG. 1 shows a perspective exploded view of a first embodiment of a bone anchoring device.
Figure 2:
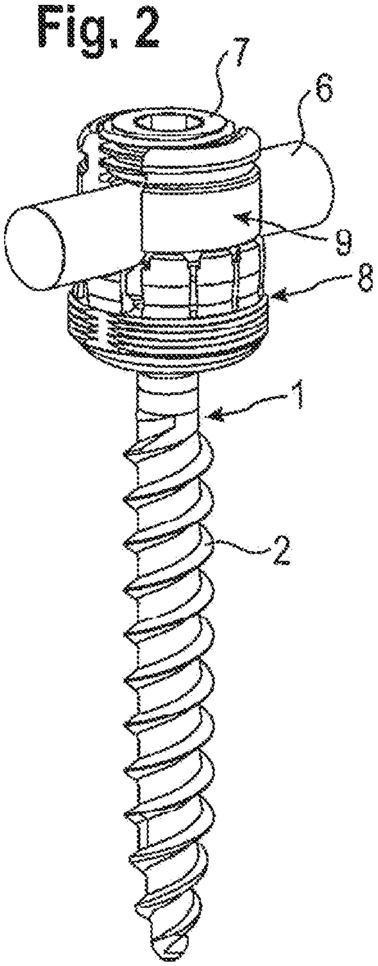
FIG. 2 shows a perspective view of the bone anchoring device of FIG. 1 in an assembled state.
Figure 3:
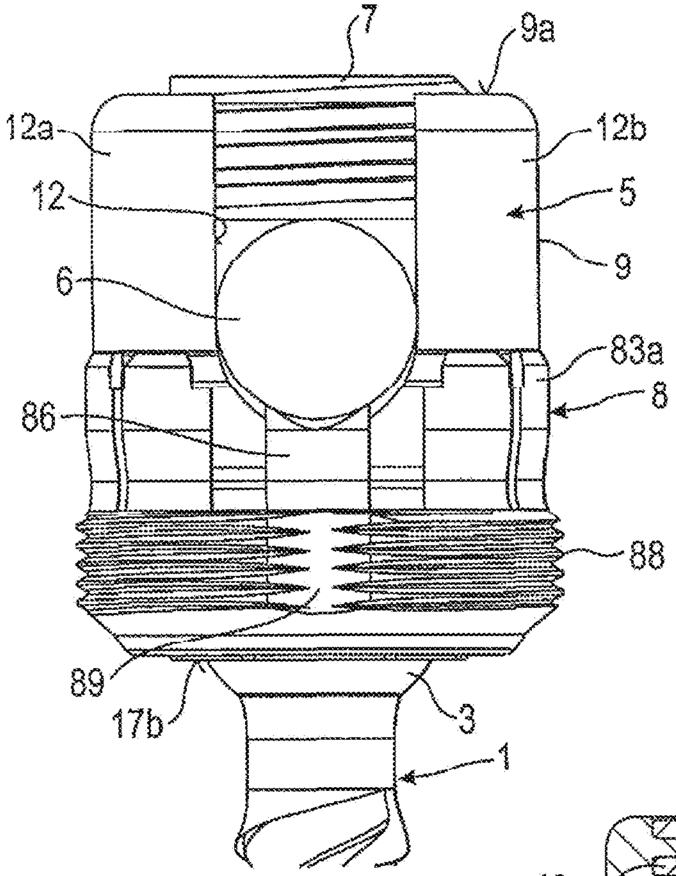
FIG. 3 shows an enlarged side view of the bone anchoring device of FIGS. 1 and 2 in the assembled state.
Figure 4:
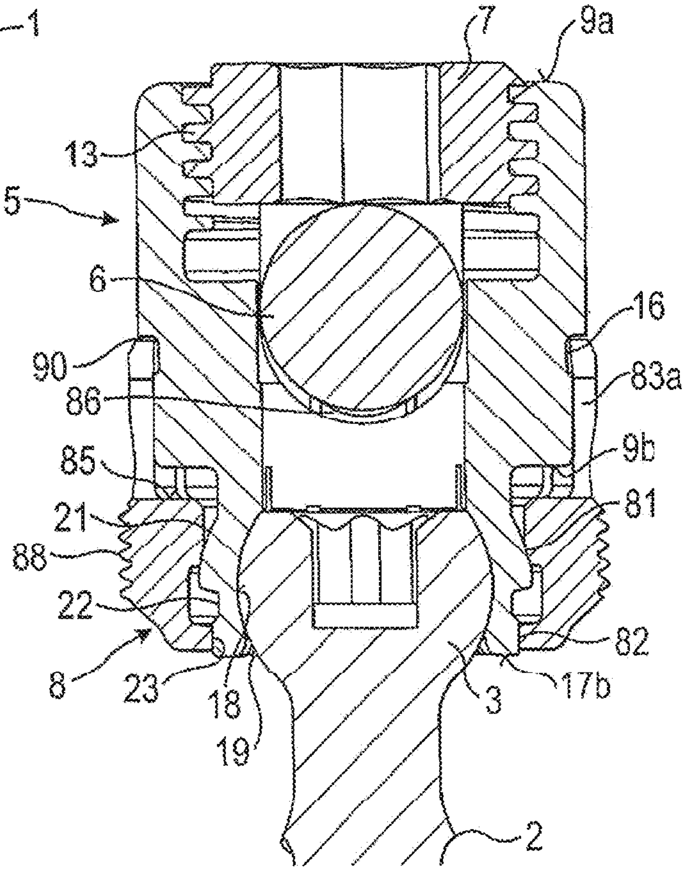
FIG. 4 shows a cross-sectional view of the bone anchoring device shown in FIG. 3, the section being taken perpendicular to an axis of an inserted rod.
Figure 5:
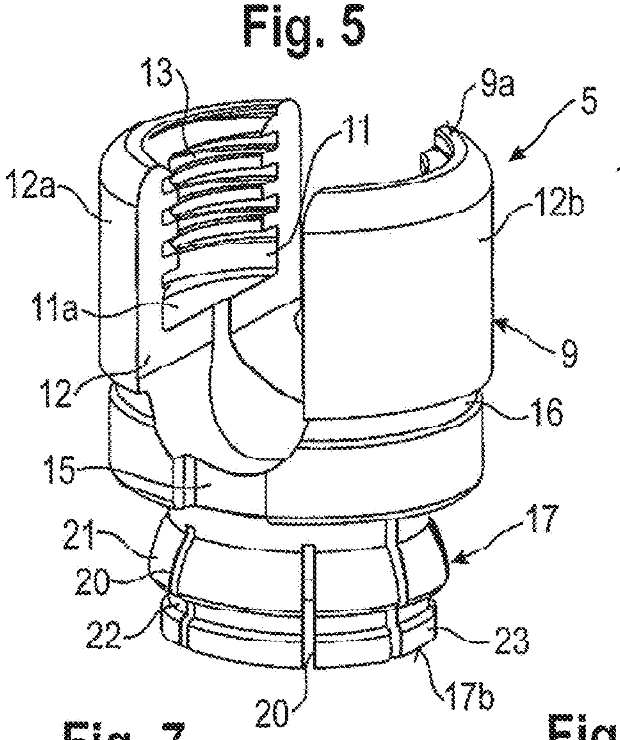
FIG. 5 shows a perspective view of a receiving part according to an embodiment of the invention.
Figure 6:
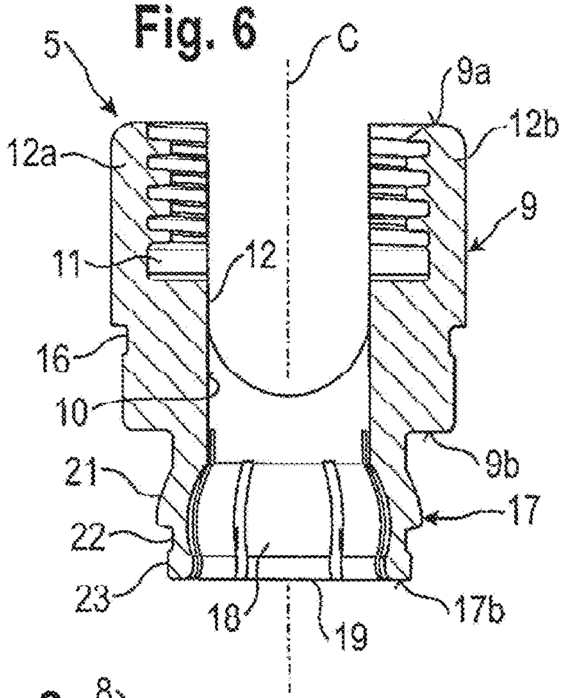
FIG. 6 shows a cross-sectional view of the receiving part of FIG. 5, the section taken perpendicular to an axis of a channel for receiving a rod.
Figure 7:
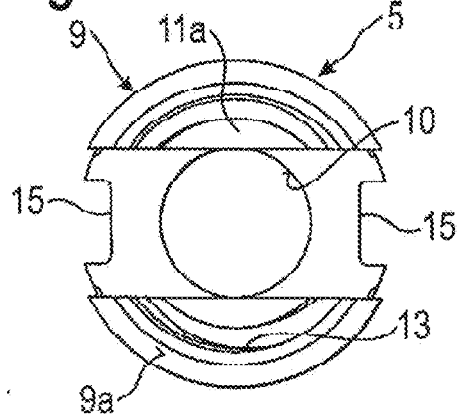
FIG. 7 shows a top view of the receiving part of FIG. 5.
Figure 8:
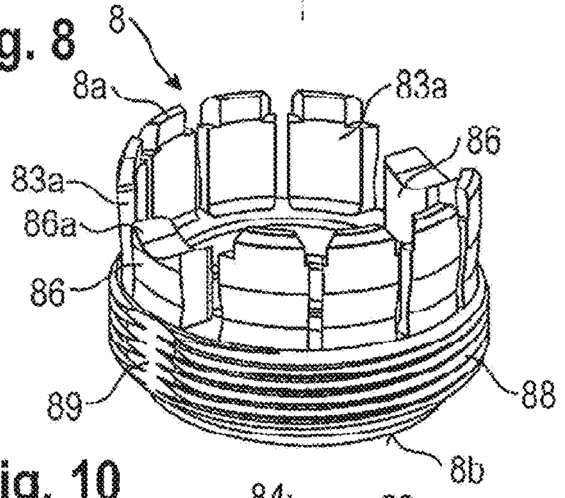
FIG. 8 shows a perspective view of a locking ring of the bone anchoring device according to the first embodiment.
Figure 9:
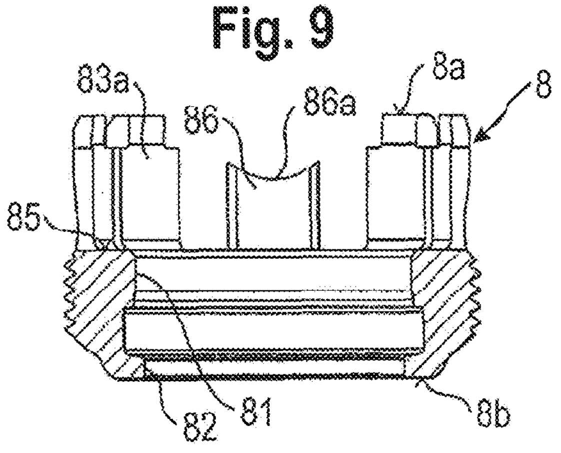
FIG. 9 shows a cross-sectional view of the locking ring of FIG. 8, the section taken perpendicular to an axis of a connected rod.
Figure 10:
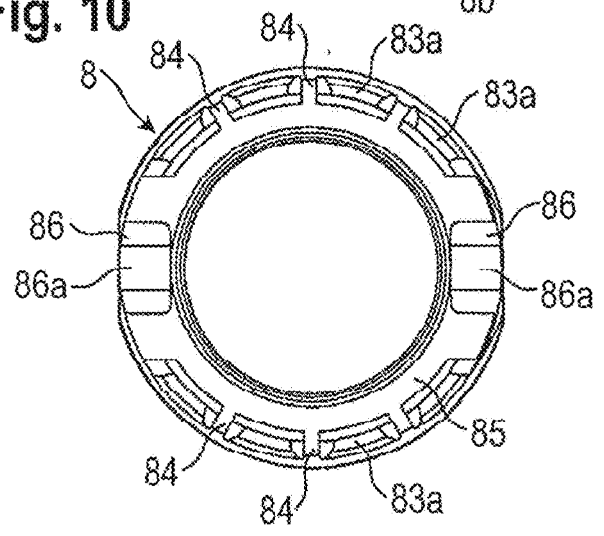
FIG. 10 shows a top view of the locking ring of FIG. 8.

As shown in FIGS. 1 and 2, a bone anchoring device according to an embodiment of the invention includes a bone anchoring element 1 in the form of, for example, a bone screw having a shank 2 with a threaded portion and a head 3 with a spherically-shaped outer surface portion. The head 3 has a recess 4 for engagement with a driver or tool. The bone anchoring device also includes a receiving part 5 for receiving a rod 6 to be connected to the bone anchoring element 1. Further, a fixation element 7 in the form of, for example, an inner screw may be provided for fixing the rod 6 in the receiving part 5. The bone anchoring device further includes a locking ring 8 for locking the head 3 in the receiving part 5.

Referring to FIGS. 1 to 7, the receiving part 5 includes a rod receiving portion 9 which may have a portion that is substantially cylindrical. The rod receiving portion 9 has a first end **9*a* and an opposite second end 9*b*, and a central axis C that passes through the first end 9*a* and the second end 9*b*. A coaxial first bore 10 is provided at the second end 9*b* as shown, for example, in FIGS. 6 and 7. A diameter of the first bore 10 is smaller than a diameter of the head 3 of the bone anchoring element 1. The rod receiving portion 9 further includes a coaxial second bore 11 extending from the first end 9*a* to a distance from the second end 9*b*. A diameter of the second bore 11 is larger than the diameter of the first bore 10. By the second bore 11, an abutment surface 11*a* is provided or formed inside the rod receiving portion 9 that may serve as an abutment for a tool, to be described in more detail below. A substantially U-shaped recess 12 extends from the first end 9*a* in the direction of the second end 9*b* in the rod receiving portion 9, wherein a width of the recess 12 is slightly larger than a diameter of the rod 6, in such a way that the rod 6 can be placed in the recess 12 and can be guided therein. By means of the recess 12, two free legs 12*a*, 12*b* are formed, on which an internal thread 13 may be provided. The internal thread 13 can be, for example, a metric thread, a flat thread, a negative angle-thread, a saw-tooth thread, or any other thread form. Preferably, a thread form such as a flat thread or a negative angle thread that prevents or reduces splaying of the legs 12*a*, 12*b* when the inner screw 7 is screwed-in is used. A depth of the recess 12, which forms a channel for the rod 6, is such that the rod 6 and the inner screw 7 can be inserted between the legs 12*a*, 12*b*. Cut-outs 15 are provided in the rod receiving portion 9, extending from the second end 9*b* to the recess 12. The cut-outs 15 are provided on either end of the channel formed by the recess 12**.

The inner screw 7 has a thread corresponding to the internal thread 13 provided on the legs **12*a*, 12*b*. If a thread form that prevents the legs from splaying is used, a single locking element such as the inner screw 7** may be sufficient.

On an outer surface of the rod receiving portion 9, in the region of the legs **12*a*, 12*b*, a groove 16 may be provided that extends in a circumferential direction and serves for engagement with a portion of the locking ring 8. The groove 16 may be asymmetric in such a way to allow for disengagement of the locking ring 8 and the groove 16 when the locking ring 8 is shifted downwards, away from the second end 9*b***.

At the side of the second end **9*b*, the receiving part 5 further includes a head receiving portion 17 providing an accommodation space for the head 3 of the bone anchoring element 1. The head receiving portion 17 has a greatest outer diameter that is smaller than a greatest outer diameter of the rod receiving portion 9. An internal hollow section 18 forms a seat for the head 3 of the bone anchoring element 1, and is open via an opening 19 to a free end 17*b* of the head receiving portion 17. The internal hollow section 18 is adapted in its shape to the shape of the head 3. In the embodiment shown, section 18 is a spherical section to accommodate spherical head 3. Furthermore, the hollow section 18 is configured to encompass the head 3 of the bone anchoring element 1 from the side, to cover a region including a largest diameter of the head 3**.

A plurality of slits 20 are provided in the head receiving portion 17 that are open to the free end 17*b*. The slits 20 render the head receiving portion 17 flexible so that the head receiving portion 17 can be compressed to clamp and finally lock an inserted head 3 in the hollow internal portion 18 by means of friction. A number and size of the slits 20 is provided depending on the desired flexibility of the head receiving portion 17. The flexibility of the head receiving portion 17 is such that the head 3 of the bone anchoring element 1 can be inserted by expanding the head receiving portion 17, and can be clamped by compressing the head receiving portion 17.

An outer surface of the head receiving portion 17 has a first section 21 with an outer diameter increasing towards the free end 17*b*, for example, in an outwardly curved or conically widening manner. Adjacent to the first section 21, there may be a circumferential groove 22 that is recessed with respect to the first section 21 and that serves for engagement with a portion of the locking ring 8. The groove 22 may be shaped so as to allow for disengagement of the locking ring 8 and the groove 22 when moving the locking ring 8 in a direction towards the free end 17*b* (or away from the first end 9*a* of the rod receiving portion). This is realized, for example, by having a lower wall of the groove 22 that is inclined towards the free end 17*b*.

Adjacent the groove 22, there is a third portion 23 of the head receiving portion 17 with a substantially cylindrical outer surface. The third portion 23 may be configured to cooperate with a portion of the locking ring 8 to enhance a clamping effect of the locking ring 8.

The locking ring 8 will now be described in particular with reference to FIGS. 3, 4, and 8 to 10. The locking ring 8 may include a portion that is substantially cylindrical, and has an upper end 8*a* and a lower end 8*b*. In a mounted state, the upper end 8*a* is oriented in the direction of the first end 9*a* of the rod receiving portion 9 and the lower end 8*b* is oriented in the direction of the free end 17*b* of the head receiving portion 17. Approximately in a central region of the locking ring 8, at an inner wall, a first portion 81 is provided that cooperates with the first outer surface portion 21 of the head receiving portion 17 to compress the head receiving portion 17. The first portion 81 may be slightly tapered, may be straight, or may be curved with a curvature directed towards a center of the locking ring 8. Furthermore, at the lower end 8*b*, the locking ring has an inwardly projecting edge 82, an inner diameter of which is smaller than inner diameters of other portions of the locking ring 8. The inwardly projecting edge 82 is configured to engage the groove 22 of the head receiving portion 17 and to finally engage the cylindrical portion 23 of the head receiving portion 17 when the bone anchoring device is in a locked state.

The locking ring 8 also has a third portion including upwardly extending wall portions 83*a* that are separated from each other by slits 84. The upwardly extending wall portions 83*a* are arranged at an outer circumference of an inner circumferential shoulder 85 of the locking ring 8, and render the third portion of the locking ring 8 flexible. A number and size of the slits 84 and a thickness of the wall portions 83*a* are configured such that a desired flexibility is obtained. At respective free ends of the wall portions 83*a*, the wall portions 83*a* are configured to engage the groove 16 provided on the outer surface of the rod receiving portion 9.

Two projections 86 that are located diametrically opposite to each other are also formed in the third portion of the locking ring 8. The projections 86 have such a height that they extend through the cut-outs 15 and project above a bottom of the substantially U-shaped recess 12 when the locking ring 8 is in a position where its shoulder 85 abuts the second end 9*b* of the rod receiving portion 9. A free end surface 86*a* of the projections 86 may be curved, for example, concave. The locking ring 8 is arranged around the head receiving portion 17 of the receiving part 5 such that the projections 86 are located at the positions of the recess 12. By means of this, the projections 86 prevent the locking ring 8 from rotating relative to the receiving part 5 when the rod 6 is not yet inserted.

The locking ring further includes on its outer surface portion adjacent the upwardly extending wall portions 83*a* an engagement portion 88 for engagement with a tool, described in more detail below. In a first embodiment, the engagement portion 88 is realized by an external thread. The thread extends in an axial direction of the locking ring 8 along a portion of the outer surface of the locking ring 8. A depth of the thread may be small, so that a violation of surrounding tissue or blood vessels can be avoided or minimized. Aligned with and just below the projections 86, the thread may be interrupted at two opposite thread-free sections 89. The thread may be, for example, flattened towards the center at the thread-free sections 89, respectively. The sections 89 may serve for applying a distraction or compression tool. The thread-free sections 89 can also be provided at other positions, or in some embodiments, more than two thread-free sections 89 can be provided.

The receiving part 5, the locking ring 8, the inner screw 7, and the bone anchoring element 1 may be made of bio-compatible materials, for example, of titanium or stainless steel, of a bio-compatible alloy such as Nitinol, or of a bio-compatible plastic material, such as PEEK (Polyetheretherketone). The parts can be made of the same or of different materials.

In an embodiment of the invention, the locking ring 8 can assume three main positions relative to the receiving part 5. In a first position (not shown), the inwardly projecting edge 82 of the locking ring 8 engages or is positioned adjacent to the groove 22 of the head receiving portion 17. In this position, the head 3 of the bone anchoring element 1 can be introduced into the internal hollow space 18 from the free end 17*b* of the head receiving portion 17. The locking ring 8 is prevented from moving further upwards towards the first end 9*a* of the rod receiving portion 9 because the shoulder 85 abuts against the second end 9*b* of the rod receiving portion 9.

In a second position, the locking ring 8 is shifted towards the free end 17*b* of the head receiving portion 17 until the flexible wall sections 83*a* snap with their free ends into the groove 16 of the rod receiving portion 9. In this position, the head 3 is not yet locked, but may be prevented from removal out of the internal hollow space 18. The head 3 may also be frictionally clamped in this state to such an extent that the bone anchoring element 1 is still movable relative to the receiving part 5 when a force, for example, a manually applied force, is applied to overcome the friction force. An example of the second position can be seen, for example, in FIGS. 21 and 22.

In a third position, the locking ring 8 is shifted further towards the free end 17*b* of the head receiving portion 17 (or away from the first end 9*a* of the rod receiving portion 9)

such that the head 3 is finally locked. In this position, the head receiving portion 17 is compressed by the locking ring 8, so that the head 3 cannot move and is fixed at an angular position with respect to the receiving part 5. Between upper ends of the flexible wall sections 83*a* and an upper wall of the groove 16 of the rod receiving portion 9 is a gap 90, as shown, for example, in FIG. 4. In the locked condition of the head 3, the locking ring 8 cannot be loosened, or may be very difficult to loosen, under normal operating conditions.

Figure 11:
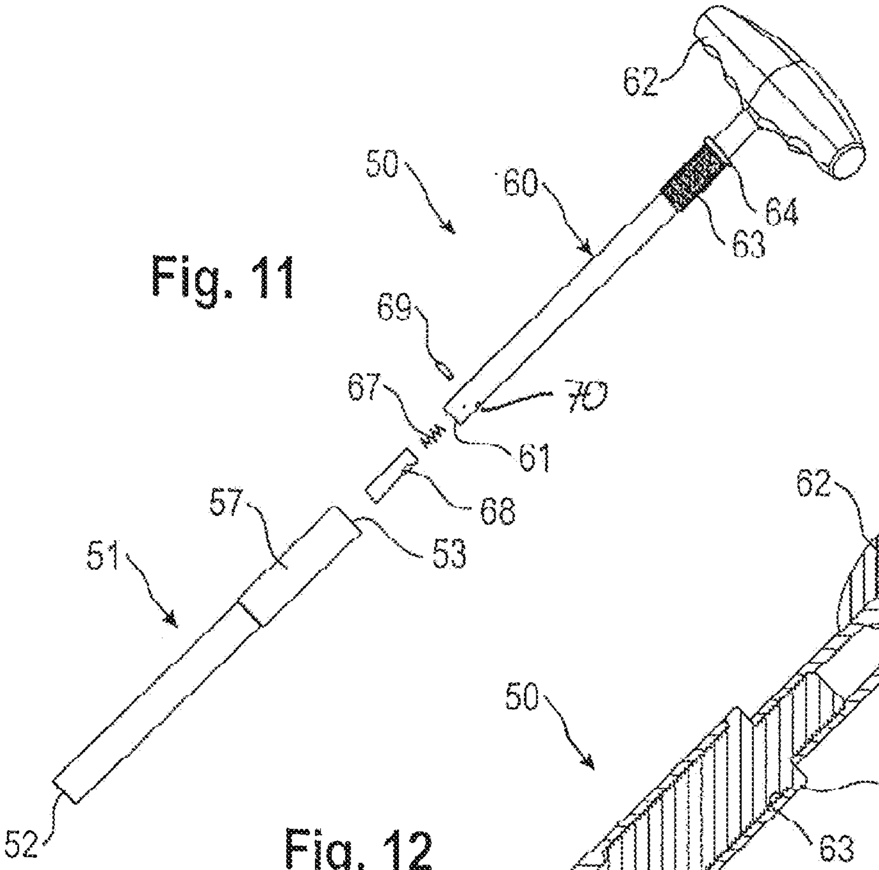
FIG. 11 shows a perspective exploded view of an embodiment of a tool that cooperates with the bone anchoring device according to the first embodiment.
Figure 12:
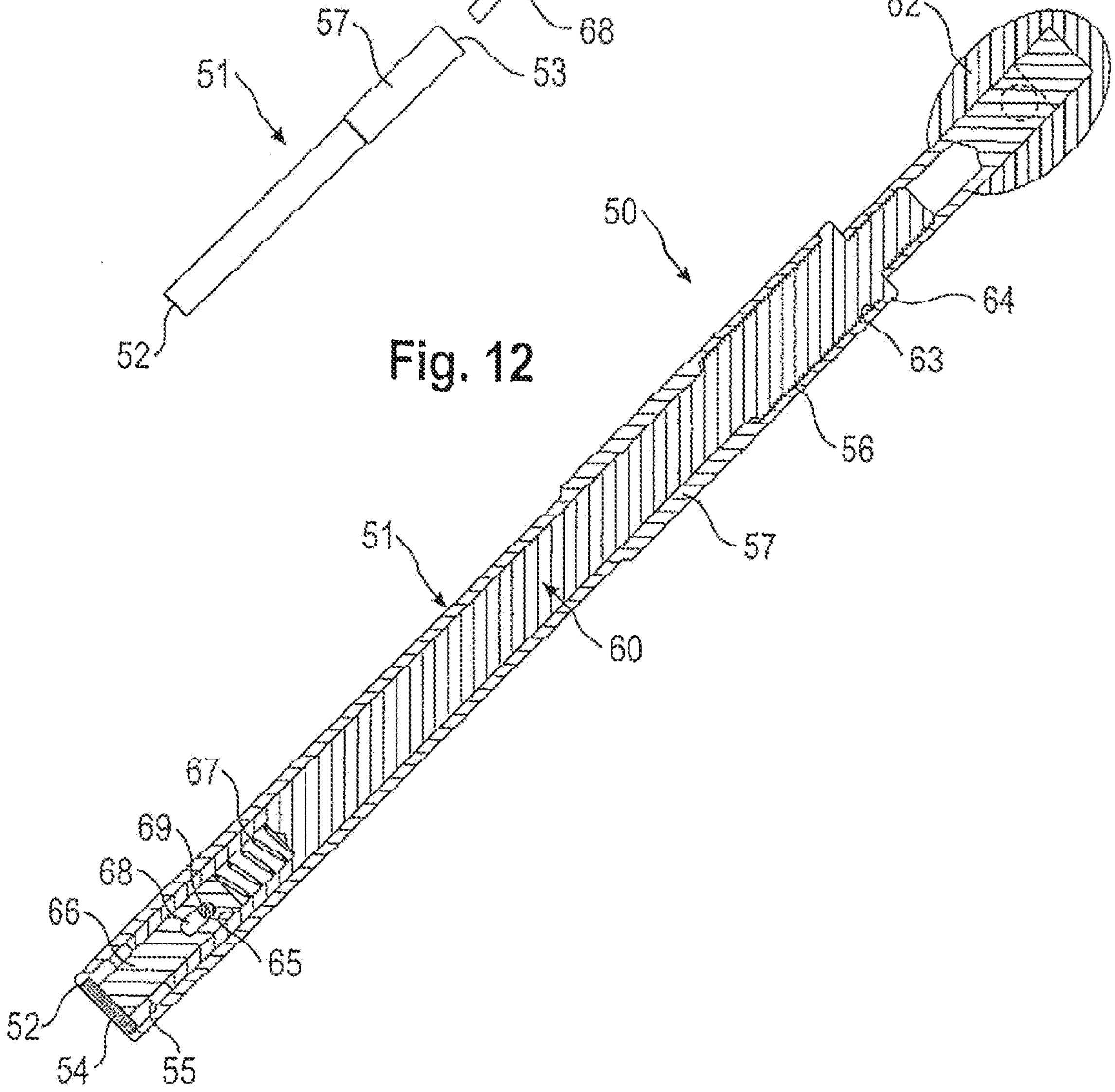
FIG. 12 shows a cross-sectional view of the tool of FIG. 11 in an enlarged view, the section taken through a central axis and perpendicular to a long side of a handle portion of the tool.

A tool 50 according to a first embodiment will now be described with reference to FIGS. 11 and 12.

Figure 14:
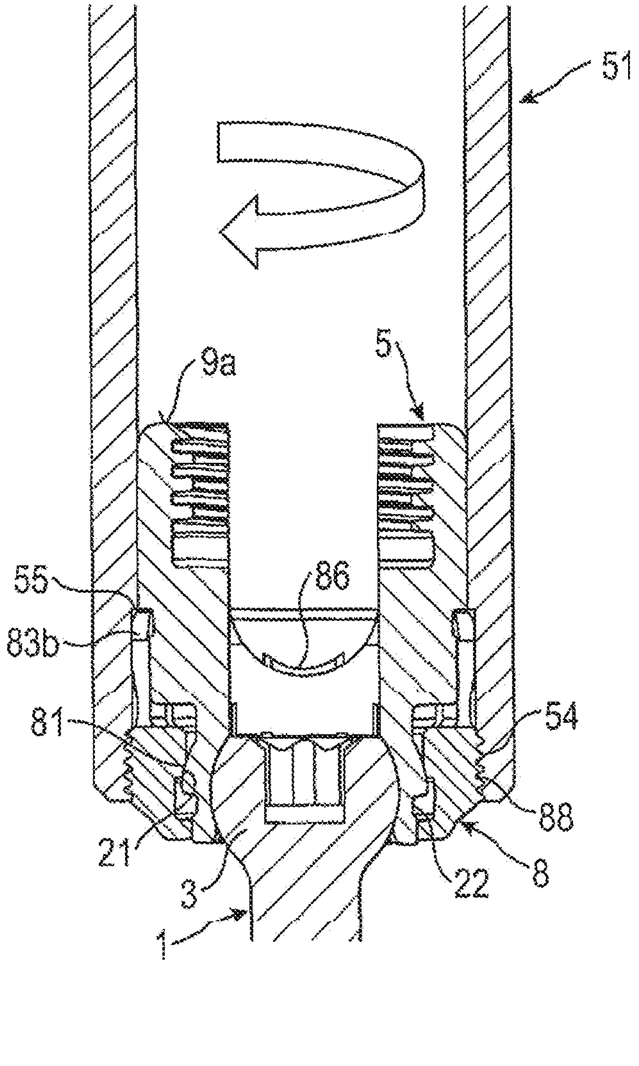
FIG. 14 shows a cross-sectional view of a further step of mounting the tool of FIGS. 11 and 12 to the bone anchoring device according to the first embodiment.

The tool 50 includes a tubular member 51 with a front end 52 and a rear end 53 opposite to the front end 52. Adjacent the front end 52, the tubular member 51 has at its inner wall an engagement portion 54 for engaging the engagement portion 88 of the locking ring 8. An inner diameter of the tubular member 51 at the front end 52 is therefore such that the tubular member 51 can be placed onto or around the receiving part 5 and can engage the locking ring 8. At a distance from the front end 52 a stop 55 is provided within the tubular member 51 that abuts against the upper edge 8*a* of the locking ring 8 when the engagement portion 54 engages the threaded portion 88, for example, as shown in FIG. 14. At its rear end 53, the tubular member 51 also has an internal threaded portion 56.

The tool 50 further includes a shaft 60 with a front end 61 and a rear end 62 that can be formed as a handle. The shaft 60 has an outer threaded portion 63 at a distance from the handle that cooperates with the internal threaded portion 56 of the tubular member 51. Adjacent the outer threaded surface portion 63 is a stop 64 that limits the insertion depth of the shaft 60 into the tubular member 51. The stop 64 can be, for example, a circumferential shoulder. The shaft 60 is insertable into the tubular member 51 and is movable therein. An insertion depth can be adjusted by the cooperation of the threads 56 and 63 of the tubular member 51 and the shaft 60, respectively. As shown in FIG. 12, when the shaft 60 is inserted and screwed into the tubular member 51 until the stop 64 abuts against the rear end 53, the front end 61 of the shaft 60 is at a distance from the front end 52 of the tubular member 51.

The shaft 60 has at its front end 61 a blind hole 65, in which a post 66 can be supported by a spring 67. An end surface 66*a* of the post 66 projects out of the front end 61 of the shaft (see, e.g., FIG. 16) and the post 66 is movable in the blind hole 65. The movement of the post 66 in the blind hole 65 may be limited in two directions by a stop. The stop may be formed by an axially elongated hole 68 that extends through the post 66 and through which a pin 69 is passed. The pin 69 extends through a transverse hole 70 provided in the shaft 60, as shown in particular in FIG. 11. By means of this, the post 66 is moveable between a first position in which the pin is at an end of the elongate hole 68 nearer to the spring 67, to a second position in which the pin 69 is at an end of the elongate hole 68 nearer to the front end 61 of the shaft 60. In the first position, the post 66 projects further outward from the front end 61 and may be biased by partial compression of the spring 67. In the second position, the post 66 is urged towards the end of the blind hole 65, thereby further compressing the spring 67. The spring 67 is shown as a helical spring, but can be any other spring or mechanism that accomplishes the same purpose. For example, the spring mechanism can also be realized by an elastomer cushion.

Figure 13:
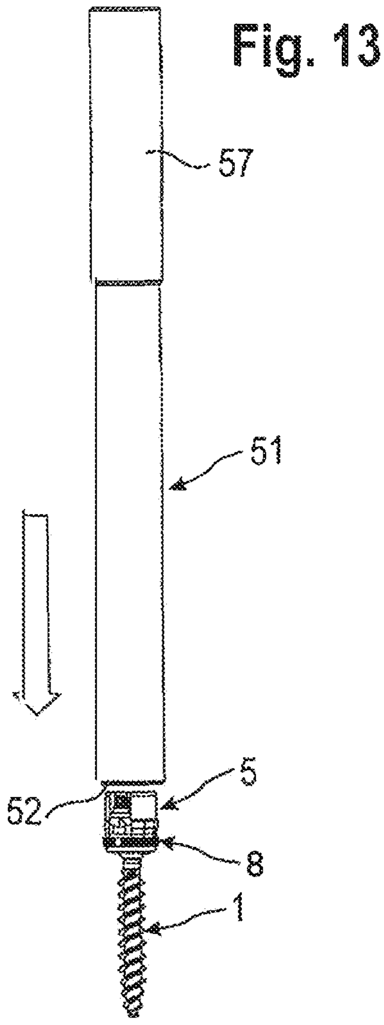
FIG. 13 shows a perspective view of a first step of mounting the tool of FIGS. 11 and 12 to the bone anchoring device of FIGS. 1 and 2.

Operation of the tool 50 will now be described with reference to FIGS. 13 to 24. First, the tubular member 51 may be separated from the shaft 60. As shown in FIGS. 13 and 14, the tubular member 51 is placed over the receiving part 5 (of a locked bone anchoring device, for example) until the threaded portion 54 engages the threaded portion 88 of the locking ring 8.

Figure 15:
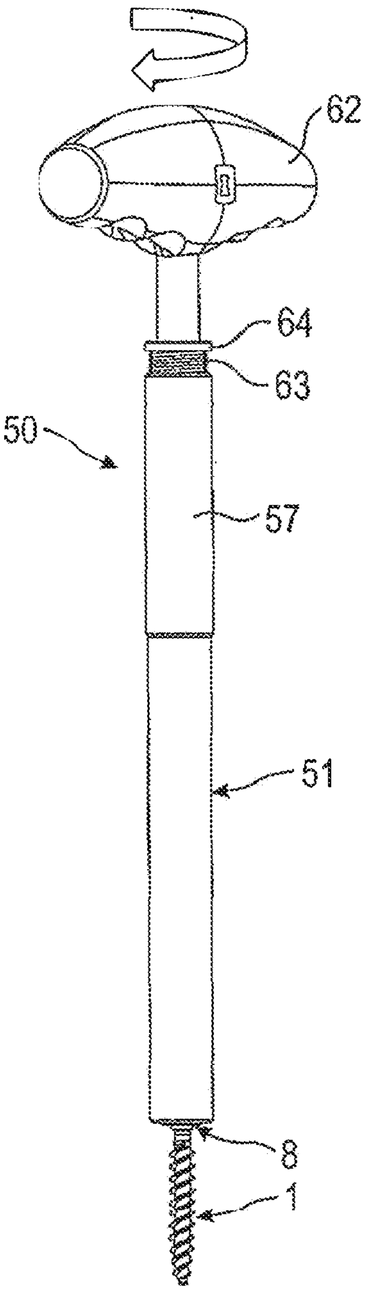
FIG. 15 shows a perspective view of a further step of mounting the tool of FIGS. 11 and 12.
Figure 16:
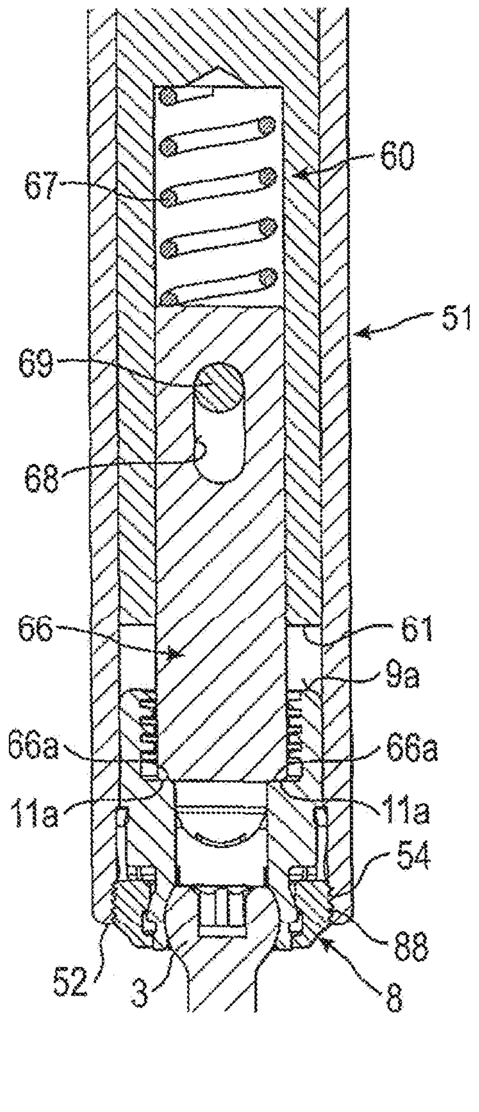
FIG. 16 shows an enlarged cross-sectional view of a portion of the tool attached to the bone anchoring device shown in FIG. 15.
Figure 20:
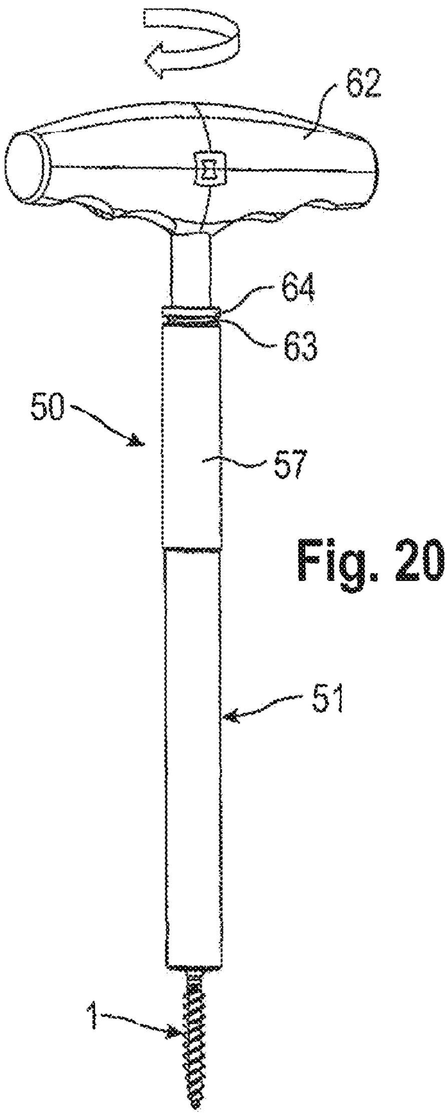
FIG. 20 shows a perspective view of a first step of releasing a locking mechanism of the bone anchoring device of FIGS. 1 and 2 with the tool of FIGS. 11 and 12.

In a next step, shown in FIGS. 15 and 16, the shaft 60 is inserted into the tubular member 51 until the front end 66*a* of the post 66 abuts against the abutment surface 11*a* in the receiving part 5 (see FIG. 16). In this position, the front end 61 of the shaft 60 is spaced apart from the first end 9*a* of the rod receiving portion 9 of the receiving part 5. The post 66 is in its first position, where the pin 69 is nearer to the spring 67. The shaft 60 is not yet fully introduced into the tubular member 51. As shown in FIGS. 17 and 18, the shaft 60 is thereafter further screwed into the tubular member 51 until the front end 61 of the shaft abuts against the first end 9*a* of the rod receiving portion 9 of the receiving part 5. Thereby, a counterforce acting onto the post 66 presses the post 66 into the blind hole 65 against the force of the spring 67. In this condition, the locking ring 8 is still in its third position, in which the head is locked. This can be seen more clearly in the enlarged representation according to FIG. 19 that shows the gap 90 between the upper end 8*a* of the locking ring 8 and the wall of the groove 16 facing the upper end 8*a*.

Figure 21:
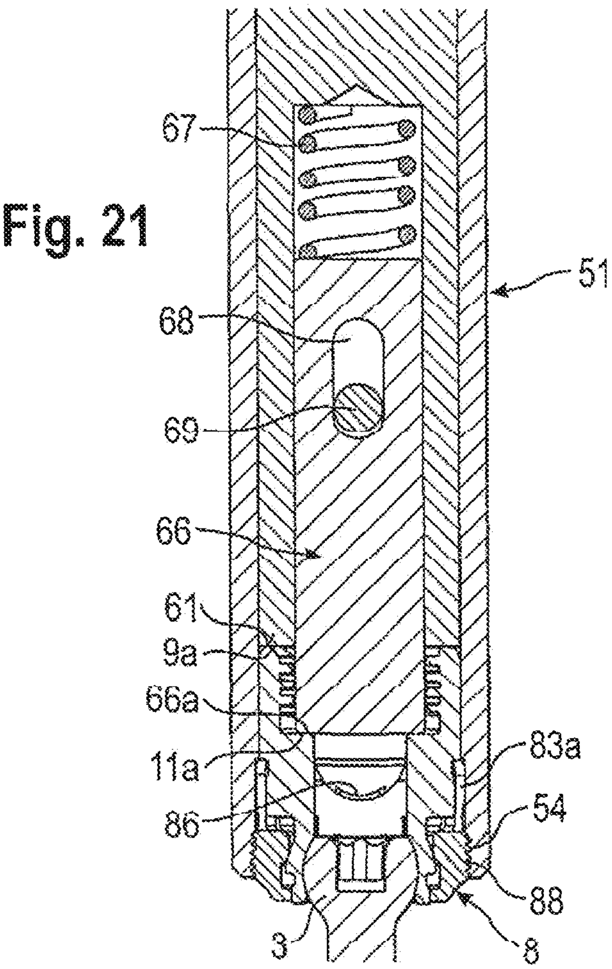
FIG. 21 shows an enlarged cross-sectional view of the tool and bone anchoring device shown in FIG. 20.

For releasing the locking ring 8 from the locking position, the tubular member 51 can be gripped at a gripping portion 57 and held in this position while the shaft 60 is further screwed into the tubular member 51, as shown in FIG. 21. By means of this, the locking ring 8 is drawn upwards (i.e., towards first end 9*a* of rod receiving portion 9) until flexible wall section 83*a* abuts the upper wall of groove 16, as shown in detail in FIG. 22. Here, the locking ring 8 is in the second position, where the locking ring 8 does not lock the head 3.

Figure 22:
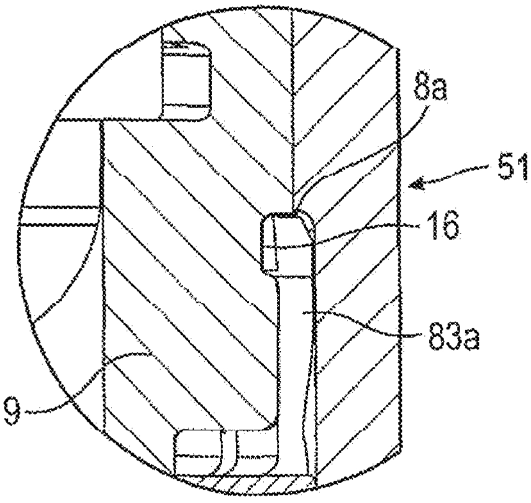
FIG. 22 shows an enlarged portion of FIG. 21.
Figure 23:
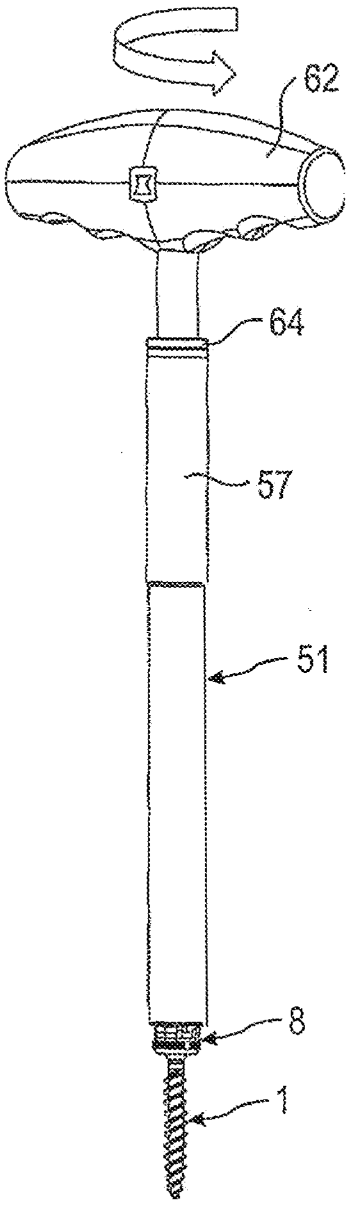
FIG. 23 shows a perspective view of a step of removing the tool of FIGS. 11 and 12 from the bone anchoring device of FIGS. 1 and 2.
Figure 24:
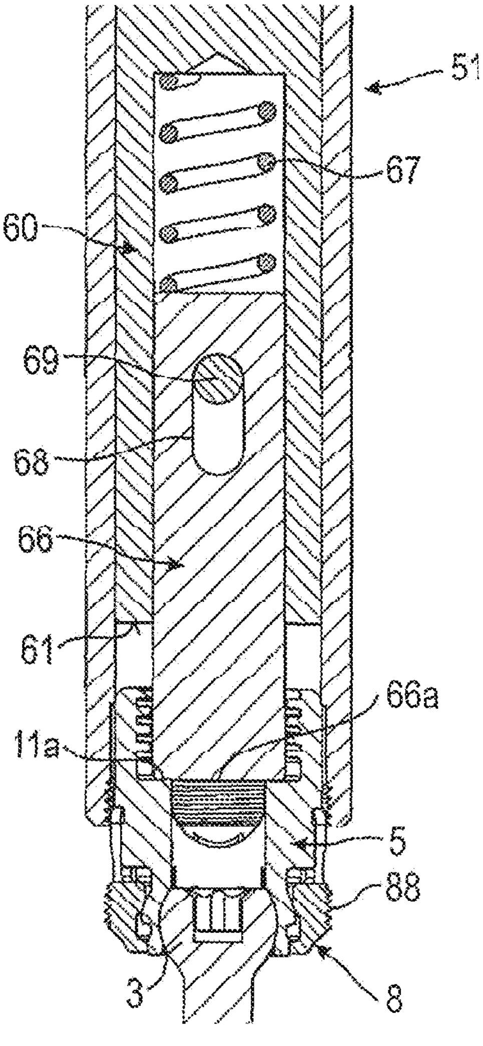
FIG. 24 shows an enlarged cross-sectional view of a portion of the tool and bone anchoring device shown in FIG. 23.
Figure 25:
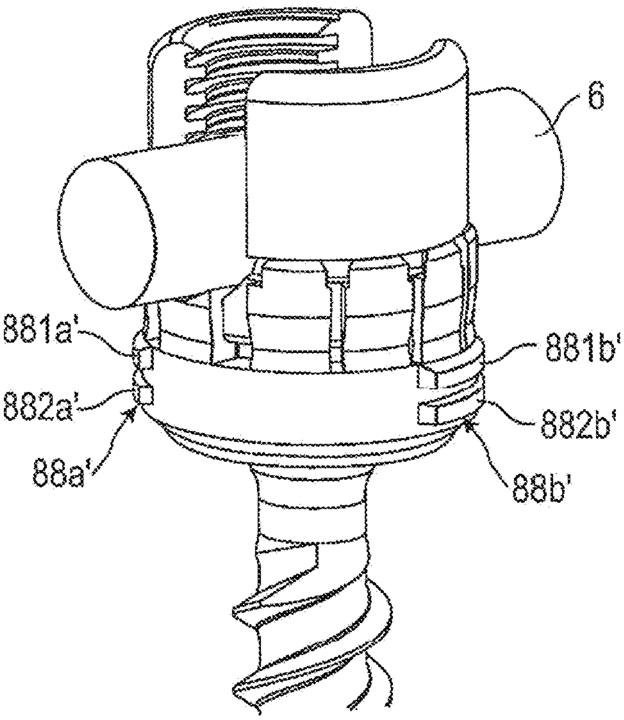
FIG. 25 shows a perspective view of a bone anchoring device according to a second embodiment in an assembled state.
Figure 26:
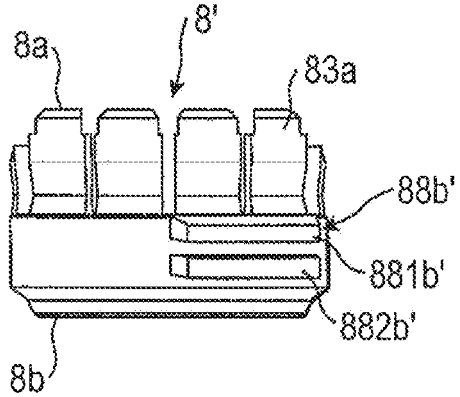
FIG. 26 shows a side view of a locking ring of the bone anchoring device according to the second embodiment shown in FIG. 25.
Figure 27:
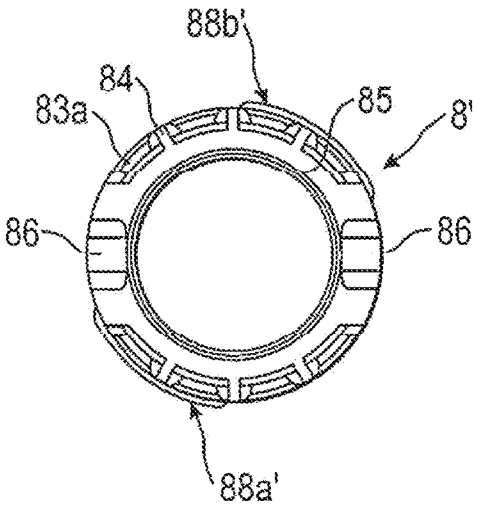
FIG. 27 shows a top view of the locking ring of FIG. 26.
Figure 28:
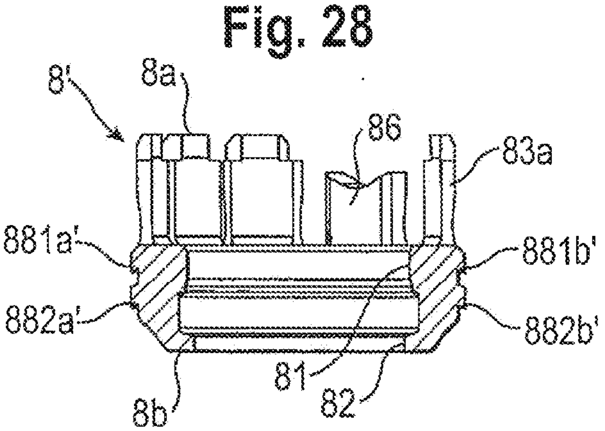
FIG. 28 shows a cross-sectional view of the locking ring of FIG. 26.

A step of removing the tool is shown in FIGS. 23 and 24. The handle at end 62 can be turned in the other or opposite direction. The locking ring 8 abuts against an end of the groove 16, as shown in FIG. 22, and therefore, it can not be drawn further upwards (e.g., back towards the insertion position). Because the post 66 abuts against the abutment surface 11*a* of the receiving part, the screwing back of the shaft 60 does not result in simultaneous rotation of the receiving part 5 and the locking ring 8. Hence, the tool 50 can be removed easily. Then, the angular position between the bone anchoring element 1 and the receiving part 5 can be readjusted.

A second embodiment of the bone anchoring device is shown in FIGS. 25 to 28. The second embodiment differs from the bone anchoring device according to the first embodiment by the design of an engagement portion of the locking ring 8'. All other parts are identical or similar to the first embodiment and are marked with the same reference numerals. The description of the same or similar parts is not repeated.

The locking ring 8' has an engagement portion for a tool that is in the form of diametrically opposite rib portions that extend circumferentially. In the embodiment shown, two rib portions 88*a*' and 88*b*' are arranged at an outer surface of the locking ring 8' beneath the elastically deformable wall portions 83*a*. The rib portions 88*a*', 88*b*' extend over a segment of an outer circumference of the locking ring 8' for approximately a quarter circle or less than a quarter circle. The rib portions 88*a*', 88*b*' may be arranged at an angle of approximately 45° with respect to the projections 86 that support the rod 6 around a circumference of the locking ring 8'.

Each rib portion 88*a*', 88*b*' includes two circumferentially extending ribs 881*a*', 882*a*' and 881*b*', 882*b*', respectively, that are spaced from each other in an axial direction of the locking ring 8'. The ribs 881*a*', 882*a*', 881*b*', 882*b*' may be slightly inclined towards the second end 8*b* of the locking ring 8', as can be seen in particular in FIG. 28. The downward inclination of the ribs 881*a'*, 882*a'*, 881*b'*, 882*b'* provide an undercut for engagement with the tool described below that enhances the safety of the engagement with the tool. In the embodiment shown, two ribs in each rib portion 88*a'*, 88*b'* are provided. It shall be noted, however, that one rib for each rib portion may be sufficient. Also, more than two ribs can be provided for each rib portion.

Figure 29:
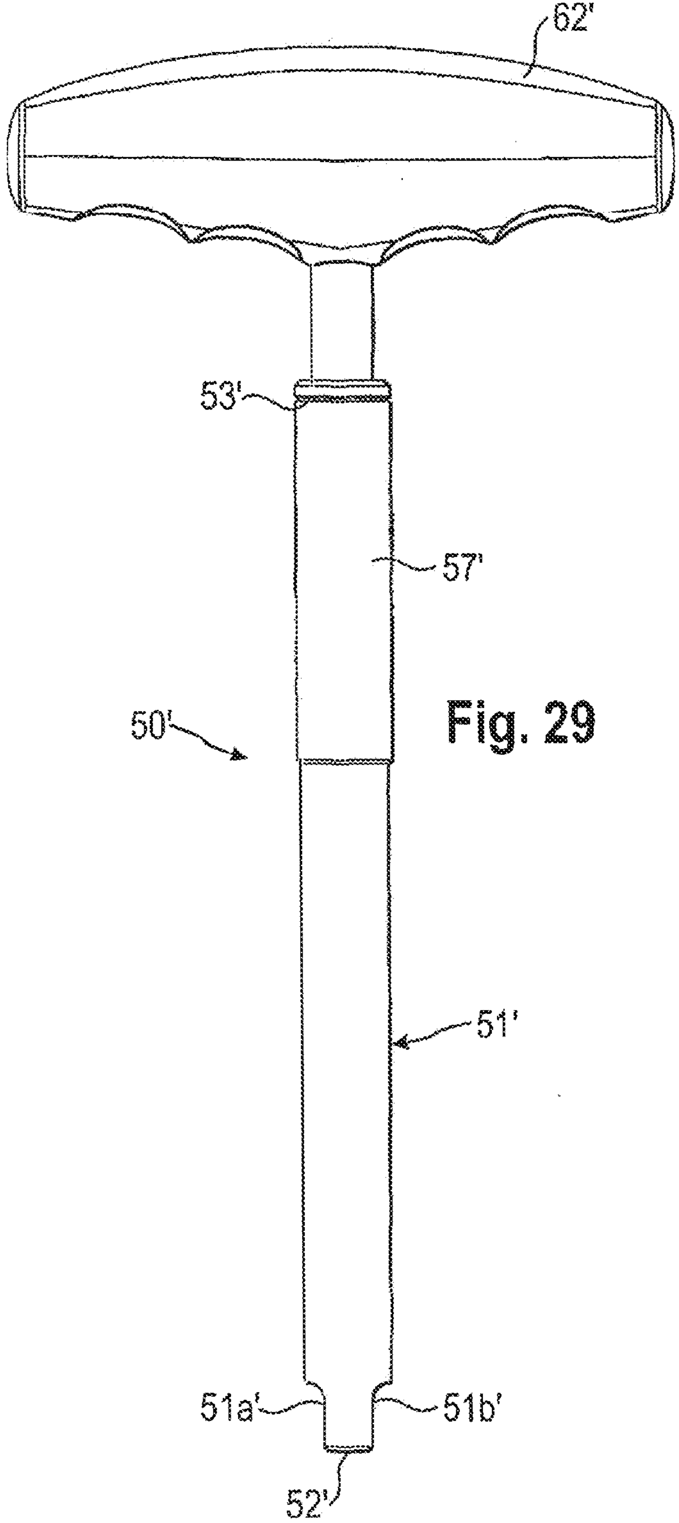
FIG. 29 shows a side view of the tool according to a second embodiment.
Figure 30:
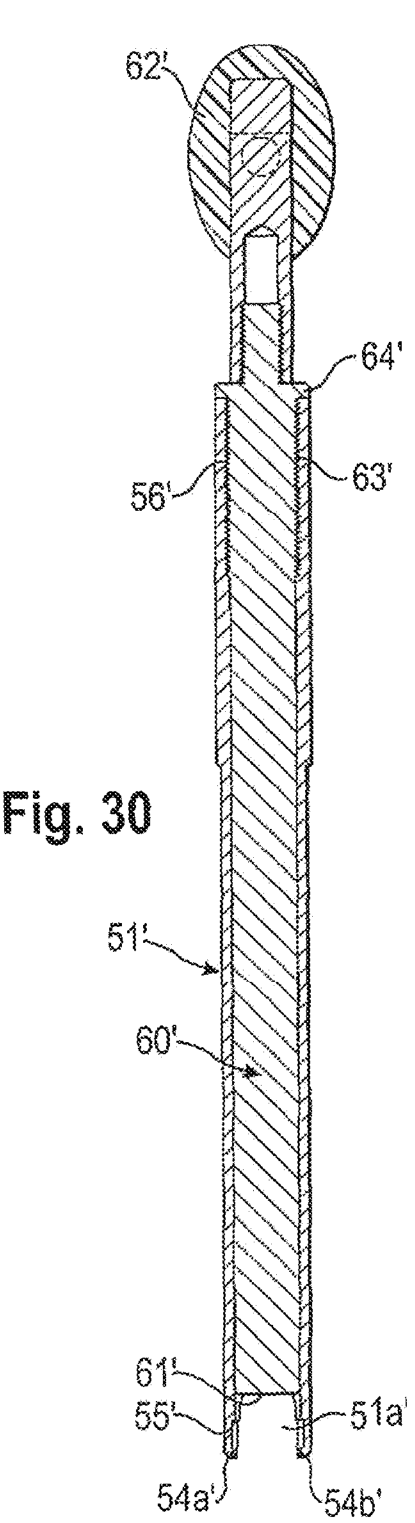
FIG. 30 shows a cross-sectional view of the tool of FIG. 29, the section taken along a central axis and perpendicular to a long side of a handle portion of the tool.

A tool for releasing the locking ring from a locked portion according to a second embodiment will be described, referring to FIGS. 29 and 30. The tool 50' includes a tubular member 51' with two substantially rectangular recesses 51*a'*, 51*b'* at a front end 52'. Adjacent the front end 52', engagement portions 54*a'*, 54*b'* that correspond to and cooperate with the rib portions 88*a'*, 88*b'* are located inside the tubular member 51'. The engagement portions 54*a'*, 54*b'* are rib portions with an inclination or bias away from the front end 52'. At a distance from the front end 52', a stop 55' is provided. The substantially rectangular recesses 51*a'*, 51*b'* have a size that may be approximately a size of rib-free portions of the locking ring in a circumferential direction, and have a depth in an axial direction that is such that when the tubular member 51' is placed onto the receiving portion and engages the locking ring 8', an inserted rod 6 can pass through the recesses 51*a'* 51*b'*.

The tubular member 51' also has a rear end 53' with an internally threaded portion 56'. At or in a vicinity of the rear end 53', a grip portion 57' is provided for facilitating gripping.

The tool 50' further includes a shaft portion 60' with a front end 61' and a rear end 62' that is provided with a handle. At a distance from the rear end 62', an externally threaded portion 63' is provided that cooperates with the internally threaded portion 56' of the tubular member 51', similarly as seen in the first embodiment. Furthermore, similar to the first embodiment, a stop in form of an annular shoulder 64' may be provided at a distance from the rear end 62'. The shaft 60' in this embodiment may not have a resiliently supported post as seen in the previous embodiment. A length of the shaft portion 60' is such that when the shaft portion 60' is inserted and screwed into the tubular member 51' until the stop 64' abuts against the rear end 53' of the tubular member 51', the recesses 51*a'*, 51*b'* at the front end 52' can cover or accommodate the receiving part 5 and the rod 6 inserted therein.

Figure 31:
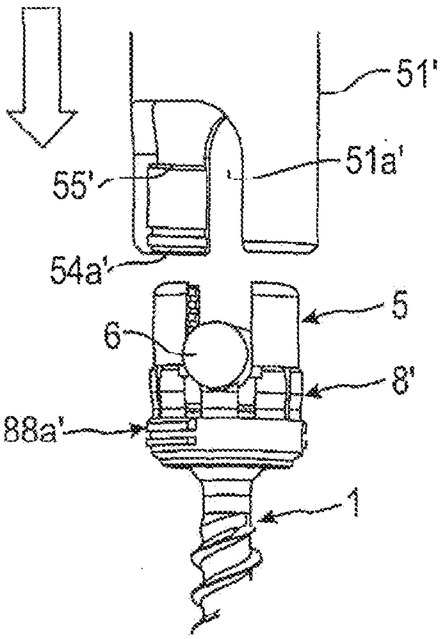
FIG. 31 shows a perspective view of a first step of mounting the tool to the bone anchoring device according to the second embodiment.
Figure 32:
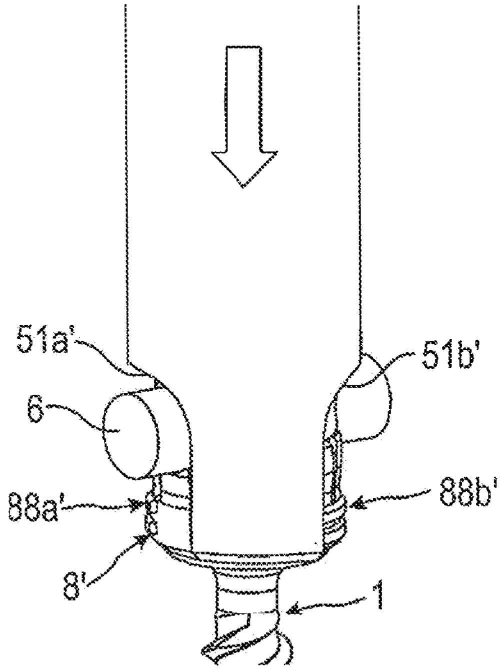
FIG. 32 shows a perspective view of a next step of mounting the tool to the bone anchoring device according to the second embodiment.
Figure 33:
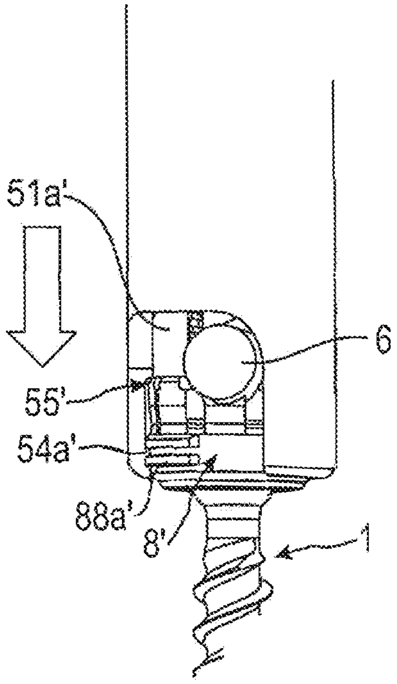
FIG. 33 shows a further step during the procedure of mounting the tool to the bone anchoring device according to the second embodiment.
Figure 34:
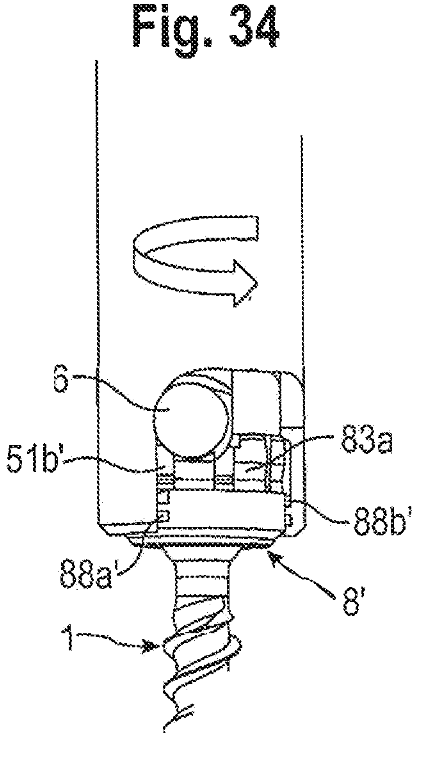
FIG. 34 shows a perspective view of a next step of mounting according to the second embodiment, wherein ribs at the locking ring are engaged by the tool.

The tool 50' according to the second embodiment can be applied, for example, when the rod 6 is inserted and the inner screw 7 is removed. As shown in FIG. 31, the tool 50' is oriented such that the engagement portion in the form of the ribs 54*a'*, 54*b'* is placed at or aligned with the rib-free portions of the locking ring 8'. The rod 6 may abut against one side of the recesses 51*a'*, 51*b'*. The tubular member 51' is shifted downwards until the stop 55' abuts against the upper edge 8*a* of the locking ring 8'. Thereafter, as shown in FIGS. 32 to 34, the tubular member 51' is rotated so that the engagement portions 54*a'*, 54*b'* inside the tubular member 51' engage the rib portions 88*a'*, 88*b'* on the outer surface of the locking ring 8'. Because the recesses 51*a'*, 51*b'* are sufficiently large in a circumferential direction, the tubular member 51' can be rotated such that the rod 6 may abut against the other side of the recesses 51*a'*, 51*b'* after rotation, as shown in FIG. 34.

Figure 35:
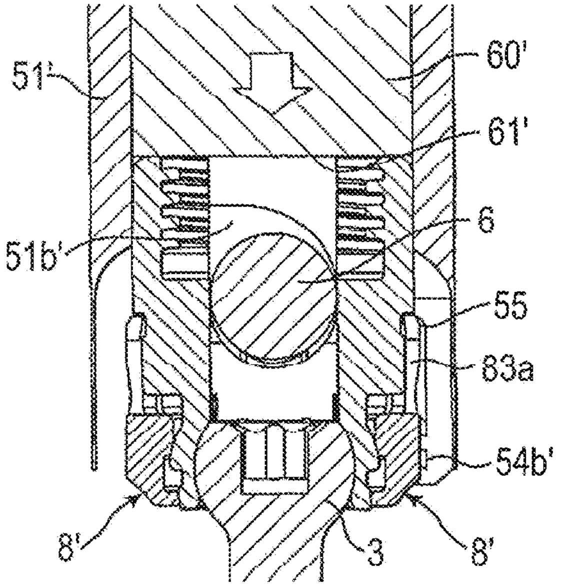
FIG. 35 shows a cross-sectional view of the bone anchoring device with the tool mounted thereon according to the second embodiment.
Figure 36:
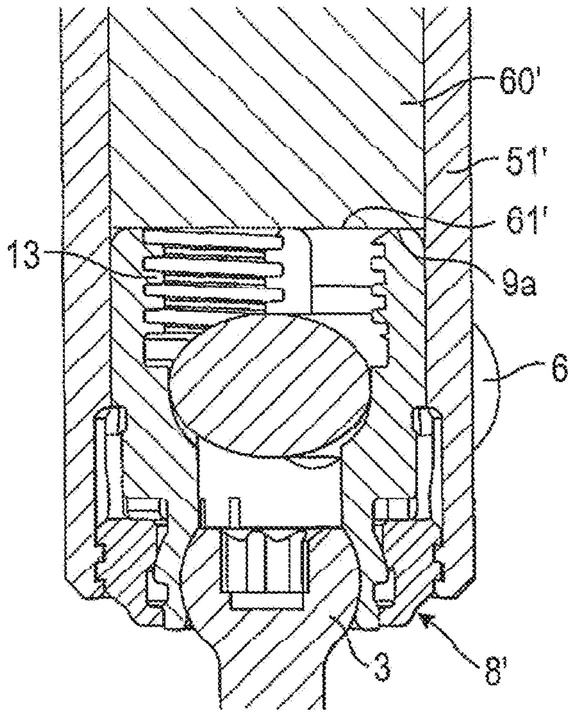
FIG. 36 shows an enlarged cross-sectional view of the device of FIG. 35 rotated by about 45°.
Figure 38:
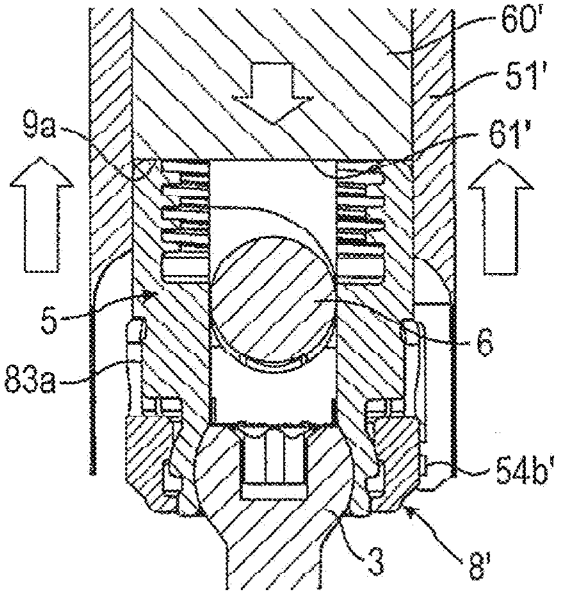
FIG. 38 shows a cross-sectional view of the bone anchoring device in a step of removing or detaching the tool according to the second embodiment.
Figure 37:
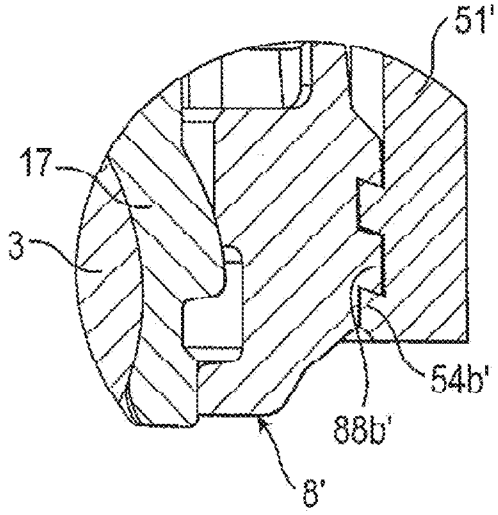
FIG. 37 shows an enlarged portion of FIG. 36.

Thereafter, as shown in FIGS. 35 to 37, the shaft 60' is screwed further into the tubular member 51' until its front end 61' abuts against the first end 9*a* of the rod receiving portion 9 of the receiving part 5. In a next step, as shown in FIG. 38, the shaft 60' is further moved into the tubular member 51' while the tubular member 51' is held at the gripping portion 57', for example, by a practitioner. By means of this, the locking ring 8' is pressed upwards (i.e. towards the first end 9*a* of the rod receiving portion 9) and is released from the locking position.

For the removal of the tool 50', the shaft 60' is slightly screwed back, then the tubular member 51' is rotated until the engagement portions 54*a'*, 54*b'* of the tubular member no longer engage the engagement portions 88*a'*, 88*b'* at the locking ring 8'. The tool 50' can then be removed by pulling the tool 50' upwards, away from the bone anchoring device.

It shall be noted that further modifications of the embodiments shown are also possible. For example, the tool according to the second embodiment may also include a post that is supported by a spring. Also, the tool according to the second embodiment may have a threaded engagement portion for engaging a threaded locking ring, similar to the first embodiment. The tool of the first embodiment may also be provided without a post.

For the engagement at the locking ring, other modifications are also conceivable. For example, it may be possible to have engagement portions with various other shapes.

The bone anchoring device according to other embodiments of the invention can be provided in a modified form. For example, the head of the bone anchoring element can have any other shape, such as, for example, a cylindrical shape, whereby a monoaxial bone screw is provided, allowing for rotation of a screw element with respect to the receiving part around a single axis. The head can also be conically shaped or otherwise shaped, with the internal hollow section of the head receiving portion adapted to the shape. In a further modification, flexibility of the head receiving portion may be based on or facilitated by properties of the material, for example, a plastic material may be used, and the slits may be fully or partly omitted.

The projections of the locking ring that engage the rod can also have various other shapes. The surface of the free end can be flat or can be otherwise shaped. The projections can be also omitted.

The head receiving portion can have an inclined open end or can be otherwise asymmetric to allow for a greater angulation of an inserted head in one direction.

The outer surface of the head receiving portion and the inner surface of the locking ring can also have other shapes that allow a compression of the locking ring by means of an increasing force when the locking ring is shifted downward.

The locking ring can also have various other designs. For example, the locking ring can be formed without the flexible wall sections.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchoring device comprising:

a bone anchoring element comprising a shank for anchoring to bone and a head;

a receiving part for coupling a rod to the bone anchoring element, the receiving part having a first end, a second end, and a central axis extending between the first and second ends, and comprising a rod receiving portion defining a U-shaped recess for receiving the rod, the recess extending from the first end towards the second end to form two free legs, and a head receiving portion at the second end for pivotably accommodating the head of the bone anchoring element; and a ring configured to be assembled to the head receiving portion from the second end of the receiving part, the ring comprising an outer surface that faces away from the central axis when the ring is assembled to the head receiving portion and a thread formed on at least part of the outer surface;

wherein when the ring is already assembled to the head receiving portion, the head is connectable to the head receiving portion from the second end of the receiving part, and the bone anchoring device is configured to assume a locking position where a compressive force is exerted on the head to lock the head relative to the receiving part.

2. The bone anchoring device of claim 1, wherein when the head is connected to the receiving part, the head is held in a seat, and wherein a surface of the seat for contacting the head is configured to be spaced apart from the ring.

3. The bone anchoring device of claim 1, wherein the ring is positionable around the head receiving portion.

4. The bone anchoring device of claim 1, wherein the ring comprises a closed ring that is configured to extend circumferentially entirely around the central axis.

5. The bone anchoring device of claim 1, wherein the thread is configured to remain completely spaced apart from the receiving part.

6. The bone anchoring device of claim 1, wherein the thread forms an engagement structure for engagement with a tool.

7. The bone anchoring device of claim 1, wherein an axial position of the ring relative to the receiving part is adjusted to assume the locking position.

8. A bone anchoring device comprising:

a bone anchoring element comprising a shank for anchoring to bone and a head;

a receiving part for coupling a rod to the bone anchoring element, the receiving part having a first end, a second end, and a central axis extending between the first and second ends, and comprising a rod receiving portion defining a U-shaped recess for receiving the rod, the recess extending from the first end towards the second end to form two free legs, and a head receiving portion at the second end for pivotably accommodating the head of the bone anchoring element; and a ring configured to be assembled to the head receiving portion, the ring comprising an outer surface that faces away from the central axis when the ring is assembled to the head receiving portion and a thread formed on at least part of the outer surface, and an inner surface that faces towards the central axis when the ring is assembled to the head receiving portion, wherein part of the inner surface that is farther away from the first end of the receiving part extends closer radially to the central axis than part of the inner surface that is closer to the first end of the receiving part;

wherein when the head and the ring are assembled to the head receiving portion, the head and the ring are configured to be spaced apart from one another, and the bone anchoring device is configured to assume a locking position where a compressive force is exerted on the head to lock the head relative to the receiving part.

9. The bone anchoring device of claim 8, wherein the ring is positionable around the head receiving portion.

10. The bone anchoring device of claim 8, wherein the thread is configured to remain completely spaced apart from the receiving part.

11. The bone anchoring device of claim 8, wherein the thread forms an engagement structure for engagement with a tool.

12. The bone anchoring device of claim 8, wherein an axial position of the ring relative to the receiving part is adjusted to assume the locking position.

13. The bone anchoring device of claim 8, wherein the head is connectable to the head receiving portion from the second end of the receiving part.

14. The bone anchoring device of claim 8, wherein the ring comprises a closed ring that is configured to extend circumferentially entirely around the central axis.

15. A bone anchoring device comprising:

a bone anchoring element comprising a shank for anchoring to bone and a head;

a receiving part for coupling a rod to the bone anchoring element, the receiving part having a first end, a second end below the first end, and a central axis extending between the first and second ends, and comprising a rod receiving portion defining a U-shaped recess for receiving the rod, the recess extending from the first end towards the second end to form two free legs, and a head receiving portion at the second end for pivotably accommodating the head of the bone anchoring element; and a ring configured to be assembled to the head receiving portion, the ring comprising an outer surface that faces away from the central axis when the ring is assembled to the head receiving portion and a thread formed on at least part of the outer surface;

wherein when the ring is already assembled to the head receiving portion, the head is connectable to the head receiving portion from the second end of the receiving part to a position where a portion of the head having a greatest diameter is positioned axially higher than at least part of the ring, and the bone anchoring device is configured to assume a locking position where a compressive force is exerted on the head to lock the head relative to the receiving part.

16. The bone anchoring device of claim 15, wherein when the head is connected to the receiving part, the head is held in a seat, and wherein a surface of the seat for contacting the head is configured to be spaced apart from the ring.

17. The bone anchoring device of claim 15, wherein the ring is positionable around the head receiving portion.

18. The bone anchoring device of claim 15, wherein the ring comprises a closed ring that is configured to extend circumferentially entirely around the central axis.

19. The bone anchoring device of claim 15, wherein the thread is configured to remain completely spaced apart from the receiving part.

20. The bone anchoring device of claim 15, wherein the thread forms an engagement structure for engagement with a tool.

21. The bone anchoring device of claim 15, wherein an axial position of the ring relative to the receiving part is adjusted to assume the locking position.

* * * * *